United States Patent
Sanghvi et al.

(10) Patent No.: US 7,214,387 B2
(45) Date of Patent: May 8, 2007

(54) SUSTAINED RELEASE FORMULATIONS OF METFORMIN

(75) Inventors: Pradeep P. Sanghvi, New Fairfield, CT (US); Sara Ketsela, Danbury, CT (US)

(73) Assignee: Penwest Pharmaceuticals Company, Danbury, CT (US)

( * ) Notice: Subject to any disclaimer, the term of this patent is extended or adjusted under 35 U.S.C. 154(b) by 650 days.

(21) Appl. No.: 10/630,239

(22) Filed: Jul. 30, 2003

(65) Prior Publication Data

US 2004/0109891 A1  Jun. 10, 2004

Related U.S. Application Data

(60) Provisional application No. 60/400,046, filed on Aug. 2, 2002.

(51) Int. Cl.
| | |
|---|---|
| A61K 9/22 | (2006.01) |
| A61K 9/20 | (2006.01) |
| A61K 9/28 | (2006.01) |
| A61K 9/36 | (2006.01) |
| A61K 9/34 | (2006.01) |
| A61K 9/32 | (2006.01) |
| A61K 9/48 | (2006.01) |
| A61K 9/14 | (2006.01) |
| A61K 9/16 | (2006.01) |

(52) U.S. Cl. .................. 424/468; 424/464; 424/465; 424/474; 424/479; 424/480; 424/481; 424/482; 424/451; 424/489; 424/490

(58) Field of Classification Search ............... None
See application file for complete search history.

(56) References Cited

U.S. PATENT DOCUMENTS

| | | | |
|---|---|---|---|
| 3,629,393 A | 12/1971 | Nakamoto et al. ......... 424/22 |
| 4,351,825 A | 9/1982 | Sothmann et al. .......... 424/19 |
| 4,828,836 A | 5/1989 | Elger et al. ................ 424/419 |
| 5,055,306 A * | 10/1991 | Barry et al. |
| 5,128,143 A * | 7/1992 | Baichwal et al. |
| 5,135,757 A | 8/1992 | Baichwal et al. ........... 424/465 |
| 5,330,767 A | 7/1994 | Yamamoto et al. ......... 424/497 |
| 5,399,358 A | 3/1995 | Baichwal et al. ........... 424/464 |
| 5,399,359 A | 3/1995 | Baichwal .................... 424/464 |
| 5,455,046 A | 10/1995 | Baichwal .................... 424/459 |
| 5,512,297 A | 4/1996 | Baichwal .................... 424/451 |
| 5,554,387 A | 9/1996 | Baichwal .................... 424/488 |
| 5,611,971 A | 3/1997 | Maedera et al. ........... 264/4.1 |
| 5,631,021 A | 5/1997 | Okada et al. ............... 424/451 |
| 5,651,990 A | 7/1997 | Takada et al. .............. 424/497 |
| 5,670,168 A | 9/1997 | Baichwal et al. ........... 424/464 |
| 5,955,106 A | 9/1999 | Moeckel et al. ............ 424/464 |
| 6,056,977 A | 5/2000 | Bhagwat et al. |
| 6,340,475 B2 | 1/2002 | Shell et al. ................. 424/469 |

FOREIGN PATENT DOCUMENTS

DE        44 32 757        3/1996

(Continued)

OTHER PUBLICATIONS

Campbell, et al., "A Clinical Evaluation of a Delayed Release Preparation of Metformin," *J Int Med Res*, vol. 1, pp. 551-556 (1973).

(Continued)

*Primary Examiner*—Humera N. Sheikh
(74) *Attorney, Agent, or Firm*—Wilmer Cutler Pickering Hale & Dorr LLP (57) ABSTRACT

The invention provides sustained release formulations of metformin or a pharmaceutically acceptable salt thereof, and methods of treating diabetes by administering to a patient a therapeutically effective amount of a sustained release formulation of metformin or a pharmaceutically acceptable salt thereof.

23 Claims, 5 Drawing Sheets

FOREIGN PATENT DOCUMENTS

| | | |
|---|---|---|
| EP | 0 360 562 A2 | 3/1990 |
| EP | 0 251 459 | 7/1992 |
| EP | 0 642 785 A2 | 3/1995 |
| EP | 0 709 085 | 5/1996 |
| EP | 0 749 751 | 12/1996 |
| EP | 0 531 497 | 8/1997 |
| EP | 0 580 428 | 10/1997 |
| WO | 97/17975 | 5/1997 |
| WO | WO-97/16172 A1 | 5/1997 |
| WO | WO-97/39050 A1 | 10/1997 |
| WO | WO-98/01117 A1 | 1/1998 |
| WO | 99/47128 | 9/1999 |
| WO | WO-01/22940 A1 | 4/2001 |
| WO | WO-93/01803 A1 | 2/2003 |

OTHER PUBLICATIONS

Pentikainen, "Bioavailability of Metformin. Comparison of solution, rapidly dissolving tablet, and three sustained release products," *Int J Clin Pharmacol, Ther and Toxicol*, vol. 4, pp. 213-220 (1986).

Abdallah, et al., "Preparation and evaluation of metformin hydrochloride controlled-release tablets," *S.T.P. Pharma*, vol. 4(1), pp. 15-20 (1988).

Karttunen, et al., "The Pharmacokinetics of metformin: a comparison of the properties of a rapid-release and sustained-release preparation," *Int J Clin Pharmacol, Ther and Toxicol*, vol. 21(1), pp. 31-36 (1983).

Mosby's GenRx, "Drug Names—Metformin Hydrochloride (3204) Categories, Brand Names, Formularies & Cost of Therapy," (1998) pp. 1-17.

Saleh, "Tablets produced under licence Do they have the same dissolution characteristics and drug content uniformity as the original ones? Example: metformin hydrochloride sustained-release tablets," *S.T.P. Pharma*, vol. 6(8), pp. 598-603 (1990).

Grdinic, et al., "Comparison of in-vitro release and renal elimination of 1-butylbiguanide from times-release oral antidiabetic preparations," *Acta Pharm. Jugoslav.*, vol. 29, pp. 215-221 (1979).

Dimitrijevic, et al., "Electro-Responsive Release From A Chondroitin Sulphate Hydrogel," *J. Pharm. Pharmacology.*, vol. 47, pp. 1058 (1995).

Karttunen, "The Influence of Pharmaceutical Formulation on the Gastrointestinal Side Effects of Metformin," *Scandinavian Society for the Study of Diabetes*, 15th Annual Meeting, Norway (1980).

Noel, "Kinetic Study of Normal and Sustained Release Dosage Forms of Metformin in Normal Subjects," *Research and Clinical Forums*, vol. 1(4), pp. 35-50 (1979).

Noel, "Kinetic Study of Normal and Sustained Release Dosage Forms of Metformin in Normal Subjects," *Journal of International Biomedical Information and Data*, vol. 1(1), pp. 9-20 (1980).

Bristol-Myers Squibb, "Glucophage XR (Metformin HCl extended-release) Tablets, Rx," *FDA Website*, (Posted Oct. 20, 2000).

"Glucophage Retard," The Role Liste (1993).

Araman, et a,, "In Vivo-In Vitro Correlation of Prolinged Release Metformin HCL Tablets Prepared with Coating Materials," *Supplement F, Supplement to Pharmaceutisch Weekblad Scientific Edition, 1st European Congress of Pharmaceutical Science*, vol. 14(5) (1992).

Stanforth, "Synergistically Interacting Heterodisperse Polysaccharides—Function in Achieving Controllable Drug Delivery," American Chemical Society (1993).

Dhopeshwarkar et al., Evaluation of Xanthan Gum in the Preparation of Sustained Release Matrix Tablets, Drug Development and Industrial Pharmacy, 19(9), 999-1017 (1993).

Supplemental European Search Report dated Jul. 4, 2006.

\* cited by examiner

SUSTAINED RELEASE FORMULATIONS OF METFORMIN

This application claims benefit of Provisional Application No. 60/400,046 filed Aug. 02, 2002.

FIELD OF THE INVENTION

The invention provides sustained release formulations of metformin or a pharmaceutically acceptable salt thereof, and methods of treating diabetes by administering to a patient a therapeutically effective amount of a sustained release formulation of metformin or a pharmaceutically acceptable salt thereof.

BACKGROUND OF THE INVENTION

Diabetes mellitus is a mammalian condition in which the amount of glucose in the blood plasma is abnormally high. Elevated glucose levels in some instances can lead to higher than normal amounts of a particular hemoglobin. This condition can be life-threatening and high glucose levels in the blood plasma (hyperglycemia) can lead to a number of chronic diabetes syndromes, for example, atherosclerosis, microangiopathy, kidney disorders or failure, cardiac disease, diabetic retinopathy and other ocular disorders, including blindness.

Diabetes mellitus is known to affect at least 10 million Americans, and millions more can unknowingly have the disease. There are two forms of the disease. In the form of this disease known as Type II, non-insulin dependent diabetes mellitus (NIDDM) or adult-onset (as opposed to juvenile diabetes or Type I), the pancreas often continues to secrete normal amounts of insulin. However, this insulin is ineffective in preventing the symptoms of diabetes which include cardiovascular risk factors such as hyperglycemia, impaired carbohydrate (particularly glucose) metabolism, glycosuria, decreased insulin sensitivity, centralized obesity hypertriglyceridemia, low HDL levels, elevated blood pressure and various cardiovascular effects attending these risk factors. Many of these cardiovascular risk factors are known to precede the onset of diabetes by as much as a decade. These symptoms, if left untreated, often lead to severe complications, including premature atherosclerosis, retinopathy, nephropathy, and neuropathy. Insulin resistance is believed to be a precursor to overt NIDDM and strategies directed toward ameliorating insulin resistance can provide unique benefits to patients with NIDDM.

Current drugs used for managing Type II diabetes and its precursor syndromes, such as insulin resistance, fall within five classes of compounds: the biguanides, thiazolidinediones, the sulfonylureas, benzoic acid derivatives and alpha-glucosidase inhibitors. The biguanides, e.g., metformin, are believed to prevent excessive hepatic gluconeogenesis. The thiazolidinediones are believed to act by increasing the rate of peripheral glucose disposal. The sulfonylureas, e.g., tolbutamide and glyburide, the benzoic acid derivatives, e.g. repaglinide, and the alpha-glucosidase inhibitors, e.g. acarbose, lower plasma glucose primarily by stimulating insulin secretion.

Among biguanides useful as diabetic therapeutic agents, metformin has proven particularly successful. Metformin is an anti-diabetic agent that acts by reducing glucose production by the liver and by decreasing intestinal absorption of glucose. It is also believed to improve the insulin sensitivity of tissues elsewhere in the body (increases peripheral glucose uptake and utilization). Metformin improves glucose tolerance in impaired glucose tolerant (IGT) subjects and NIDDM subjects, lowering both basal and postprandial plasma glucose.

Unlike sulfonylureas, metformin does not produce hypoglycemia in either diabetic or non-diabetic subjects. With metformin therapy, insulin secretion remains unchanged while fasting insulin levels and day-long plasma insulin response can decrease. Metformin also has a favorable effect on serum lipids, which are often abnormal in NIDDM patients. In clinical studies, particularly when baseline levels of lipids were abnormally elevated, metformin lowered mean fasting serum triglycerides, total cholesterol, and LDL cholesterol levels and had no adverse effects on other lipid levels.

There is a need in the art for new formulations of metformin that are therapeutically effective in treating diabetes. The invention is directed to this, as well as other, important ends.

SUMMARY OF THE INVENTION

The invention provides sustained release formulations of metformin or a pharmaceutically acceptable salt thereof. The sustained release formulations comprise a sustained-release delivery system. The invention also provides methods of treating diabetes and related diseases using sustained release formulations of metformin or a pharmaceutically acceptable salt thereof. These and other aspects of the invention are described herein.

DETAILED DESCRIPTION OF THE INVENTION

The invention provides compositions comprising metformin or a pharmaceutically acceptable salt thereof and a sustained release delivery system. The sustained release delivery system comprises (1) at least one hydrophilic compound, at least one cross-linking agent, and at least one pharmaceutical diluent; (2) at least one hydrophilic compound, at least one cross-linking agent, at least one pharmaceutical diluent, and at least one hydrophobic polymer; (3) at least one hydrophilic compound, at least one cross-linking agent, at least one pharmaceutical diluent, and at least one cationic cross-linking agent; (4) at least one hydrophilic compound, at least one cross-linking agent, at least one pharmaceutical diluent, at least one cationic cross-linking compound, and at least one hydrophobic polymer; (5) at least one hydrophilic compound, at least one cationic cross-linking compound, and at least one pharmaceutical diluent; or (6) at least one hydrophilic compound, at least one cationic cross-linking compound, at least one pharmaceutical diluent, and at least one hydrophobic compound.

In one embodiment, the sustained release delivery system comprises at least one hydrophilic compound, at least one cross-linking agent, at least one pharmaceutical diluent, and at least one cationic cross-linking agent.

In another embodiment, the sustained release delivery system comprises at least one hydrophilic compound, at least one cross-linking agent, at least one pharmaceutical diluent, at least one cationic cross-linking compound, and at least one hydrophobic polymer.

Metformin or a pharmaceutically acceptable salt thereof can be homogeneously dispersed in the sustained release delivery system. The metformin or the pharmaceutically acceptable salt thereof can be present in the composition in an amount of about 1 milligram to about 2000 milligrams; in an amount of about 100 milligrams to about 1000 milligrams; in an amount of about 300 milligrams to about 700 milligrams; or in an amount of about 500 milligrams.

Metformin can also be called N,N-dimethylimidodicarbonimidicdiamide; 1,1-dimethylbiguanide; N,N-dimethylbiguanide; N,N-dimethyldiguanide; or N'-dimethylguanylguanidine; and is represented by the chemical structure:

Metformin can be in the form of any pharmaceutically acceptable salt known in the art. Exemplary pharmaceutically acceptable salts include hydrochloric, sulfuric, nitric, phosphoric, hydrobromic, maleric, malic, ascorbic, citric, tartaric, pamoic, lauric, stearic, palmitic, oleic, myristic, lauryl sulfuric, napthalinesulfonic, linoleic, linolenic acid, and the like.

In one embodiment, the pharmaceutically acceptable salt of metformin is the hydrochloride salt, represented by the chemical structure:

Methods for preparing metformin and pharmaceutically acceptable salts thereof are known in the art and are described, for example, in U.S. Pat. Nos. 3,174,901 and 6,031,004, the disclosures of which are incorporated by reference herein in their entirety.

The sustained release delivery system comprises at least one hydrophilic compound. The hydrophilic compound preferably forms a gel matrix that releases metformin at a sustained rate upon exposure to liquids. "Liquids" includes, for example, gastrointestinal fluids, aqueous solutions (such as those used for in vitro dissolution testing), and mucosas (e.g., of the mouth, nose, lungs, esophagus, and the like). The rate of release of metformin from the gel matrix depends on the drug's partition coefficient between the components of the gel matrix and the aqueous phase within the gastrointestinal tract. The sustained release delivery system generally comprises the hydrophilic compound in an amount of about 2% to about 80% by weight; in an amount of about 5% to about 60% by weight; in an amount of about 10% to about 50% by weight; in an amount of about 20% to about 40% by weight, or in an amount of about 28% by weight.

The hydrophilic compound can be any known in the art. Exemplary hydrophilic compounds include gums, cellulose ethers, acrylic resins, polyvinyl pyrrolidone, protein-derived compounds, and mixtures of two or more thereof. Exemplary gums include heteropolysaccharide gums and homopolysaccharide gums, such as xanthan, tragacanth, pectins, acacia, karaya, alginates, agar, carrageenan, and gellan gums. Exemplary cellulose ethers include hydroxyalkyl celluloses and carboxyalkyl celluloses. Preferred cellulose ethers include hydroxyethyl celluloses, hydroxypropyl celluloses, hydroxypropylmethyl-celluloses, carboxy methylcelluloses, and mixtures thereof. Exemplary acrylic resins include polymers and copolymers of acrylic acid, methacrylic acid, methyl acrylate and methyl methacrylate. In one embodiment, the hydrophilic compound is a gum, more preferably a heteropolysaccharide gum, most preferably a xanthan gum, a derivative thereof, or a mixture thereof. Derivatives of xanthan gum include, for example, deacylated xanthan gum, the carboxymethyl esters of xanthan gum, and the propylene glycol esters of xanthan gum.

The sustained release delivery system can further comprise at least one cross-linking agent. The cross-linking agent is preferably a compound that is capable of cross-linking the hydrophilic compound to form a gel matrix in the presence of liquids. The sustained release delivery system comprises the cross-linking agent in an amount of about 5% to about 80% by weight; in an amount of about 10% to about 75% by weight; in an amount of about 15% to about 70% by weight; in an amount of about 20% to about 60% by weight; or in an amount of about 42% by weight.

Exemplary cross-linking agents include homopolysaccharides. Exemplary homopolysaccharides include galactomannan gums, such as guar gum, hydroxypropyl guar gum, and locust bean gum. In one embodiment, the cross-linking agent is a locust bean gum, a guar gum, or a mixture thereof. In a preferred embodiment, the cross-linking agent is locust bean gum. In another embodiment, the cross-linking agent is alginic acid, an alginic acid derivative, a hydrocolloid, or a mixture of two or more thereof.

When the sustained release delivery system comprises at least one hydrophilic compound and at least one cross-linking agent, the total amount of hydrophilic compound and cross-linking agent can be from about 25% to about 95% by weight; from about 40% to about 90% by weight; from about 50% to about 85% by weight; from about 60% to about 80% by weight; from about 65% to about 75% by weight; or about 70% by weight. When the sustained release delivery system comprises at least one hydrophilic compound and at least one cross-linking agent, the weight ratio of metformin to hydrophilic compound/cross-linking agent is generally in the range of about 1:0.1 to about 1:2, in the range of about 1:0.2 to about 1:1.5; in the range of about 1:0.3 to about 1:1; or in the range of about 1:0.5 to about 1:1.

The sustained release delivery system of the invention can further comprise one or more cationic cross-linking compounds. The cationic cross-linking compound can be used instead of or in addition to the cross-linking agent. The cationic cross-linking compounds can be used in an amount sufficient to cross-link the hydrophilic compound to form a gel matrix in the presence of liquids. The cationic cross-linking compound is present in the sustained release delivery system in an amount of about 0.5% to about 30% by weight; in an amount of about 5% to about 20% by weight; or in an amount of about 10% by weight.

Exemplary cationic cross-linking compounds include monovalent metal cations, multivalent metal cations, and inorganic salts, including alkali metal and/or alkaline earth metal sulfates, chlorides, borates, bromides, citrates, acetates, lactates, and mixtures of two or more thereof. For example, the cationic cross-linking compound can be one or more of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, or mixtures of two or more thereof. In one embodiment, the cationic cross-linking agent is calcium sulfate.

When the sustained release delivery system comprises at least one hydrophilic compound and at least one cationic cross-linking compound, the ratio of hydrophilic compound to cationic cross-linking compound can be from about 1:9 to about 9:1, from about 1:4 to about 4:1; or about 2.8:1.

Two properties of compounds (e.g., the at least one hydrophilic compound and the at least one cross-linking agent; the at least one hydrophilic compound and at least one cationic cross-linking compound; or the at least one hydrophilic compound, the at least one cross-linking agent, and the at least one cationic cross-linking compound) that form a gel matrix upon exposure to liquids are fast hydration of the compounds and a gel matrix having a high gel strength. These two properties, which are needed to achieve a slow release gel matrix are maximized in the invention by the particular combination of compounds (e.g., the at least one hydrophilic compound and the at least one cross-linking agent; the at least one hydrophilic compound and at least one cationic cross-linking compound; or the at least one hydrophilic compound, the at least one cross-linking agent, and the at least one cationic cross-linking compound). For example, hydrophilic compounds (e.g., xanthan gum) have excellent water-wicking properties which provide fast hydration. The combination of hydrophilic compounds with materials that are capable of cross-linking the rigid helical ordered structure of the hydrophilic compound (e.g., cross-linking agents, such as locust bean gum, and/or cationic cross-linking compounds, such as calcium sulfate) act synergistically to provide an unexpectedly high viscosity (i.e., high gel strength) of the gel matrix.

The sustained release delivery system can further comprise one or more pharmaceutical diluents known in the art. Exemplary pharmaceutical diluents include monosaccharides, disaccharides, polyhydric alcohols and mixtures of two or more thereof. Preferred pharmaceutical diluents include, for example, starch, lactose, dextrose, mannitol, sucrose, microcrystalline cellulose, sorbitol, xylitol, fructose, and mixtures of two or more thereof. In other embodiments, the pharmaceutical diluent is water-soluble, such as lactose, dextrose, mannitol, sucrose, or mixtures of two or more thereof. The sustained release delivery system comprises one or more pharmaceutical diluents in an amount of about 5% to about 80% by weight; from about 10% to about 50% by weight; or about 20% by weight. The ratio of pharmaceutical diluent to hydrophilic compound is generally from about 1:8 to about 8:1; or from about 1:4 to about 4:1.

The sustained release delivery system of the invention can further comprise one or more hydrophobic polymers. The hydrophobic polymers can be used in an amount sufficient to slow the hydration of the hydrophilic compound without disrupting it. For example, the hydrophobic polymer can be present in the sustained release delivery system in an amount of about 0.5% to about 20% by weight; in an amount of about 2% to about 10% by weight; in an amount of about 3% to about 7% by weight; or in an amount of about 5% by weight.

Exemplary hydrophobic polymers include alkyl celluloses (e.g., $C_{1-6}$ alkyl celluloses, carboxymethylcellulose), other hydrophobic cellulosic materials or compounds (e.g., cellulose acetate phthalate, hydroxypropylmethylcellulose phthalate), polyvinyl acetate polymers (e.g., polyvinyl acetate phthalate), polymers or copolymers derived from acrylic and/or methacrylic acid esters, zein, waxes, shellac, hydrogenated vegetable oils, and mixtures of two or more thereof. In one embodiment, the hydrophobic polymer is methyl cellulose, ethyl cellulose or propyl cellulose, or a mixture of two or more thereof. In another embodiment, the hydrophobic polymer is ethyl cellulose.

The compositions of the invention can be further admixed with one or more wetting agents (e.g., polyethoxylated castor oil, polyethoxylated hydrogenated castor oil, polyethoxylated fatty acid from castor oil, polyethoxylated fatty acid from hydrogenated castor oil, or a mixture of two or more thereof) one or more lubricants (e.g., magnesium stearate, sodium stearyl fumarate), one or more glidants (e.g., silicon dioxide), one or more buffering agents, one or more colorants, and/or other conventional ingredients.

The compositions of the invention can be in the form of orally administrable solid dosage compositions. Exemplary orally administrable solid dosage compositions include tablets, capsules comprising a plurality of granules, sublingual tablets, powders, and granules. In one embodiment, the orally administrable solid dosage compositions is a tablet. The tablets can be coated or uncoated. The coating on the tablet can be a sustained release coating.

The sustained release delivery system in the compositions of the invention can be prepared by dry granulation or wet granulation, before metformin is added, although the components can be held together by an agglomeration technique to produce an acceptable product. In the wet granulation technique, the components (e.g., hydrophilic compounds, cross-linking agents, pharmaceutical diluents, cationic cross-linking compounds, hydrophobic polymers, etc.) can be mixed together and then moistened with one or more liquids (e.g., water, propylene glycol, glycerol, alcohol) to produce a moistened mass which is subsequently dried. The dried mass can then be milled with conventional equipment into granules of the sustained release delivery system. Thereafter, the sustained release delivery system can be mixed in the desired amounts with metformin and, optionally, one or more additional sustained-release delivery components, one or more wetting agents, one or more lubricants, one or more buffering agents, one or more coloring agents, or other conventional ingredients, to produce a granulated composition. The sustained release delivery system and metformin can be blended with, for example, a high shear mixer. Metformin is generally finely and homogeneously dispersed in the sustained release delivery system. The granulated composition, in an amount sufficient to make a uniform batch of tablets, can be subjected to tableting in a conventional production scale tableting machine at normal compression pressures, e.g., about 2,000–16,000 psi. The mixture should not be compressed to a point where there is subsequent difficulty with hydration upon exposure to liquids. Methods for preparing sustained release delivery systems are described in U.S. Pat. Nos. 4,994,276, 5,128,143, 5,135,757, 5,455,046, 5,512,297 and 5,554,387, the disclosures of which are incorporated by reference herein in their entirety.

The average particle size of the granulated composition is from about 50 microns to about 800 microns, preferably from about 185 microns to about 400 microns. The average density of the granulated composition is from about 0.2 g/ml to about 0.8 g/ml, preferably from about 0.4 g/ml to about 0.7 g/ml. The tablets formed from the granulations are generally from about 2 to about 18 kp hardness; or from about 6 to about 12 kp hardness. The average flow of the granulations are from about 20 to about 50 g/sec.

In other embodiments, the invention provides sustained release coatings over an inner core comprising metformin. For example, the inner core comprising metformin can be coated with a sustained release film which, upon exposure to liquids, releases metformin from the core at a sustained rate.

In one embodiment, the sustained release coating comprises at least one water insoluble compound. The water insoluble compound can be a hydrophobic polymer. The hydrophobic polymer can be the same as or different from the hydrophobic polymer used in the sustained release delivery system. Exemplary hydrophobic polymers include alkyl celluloses (e.g., $C_{1-6}$ alkyl celluloses, carboxymethylcellulose), other hydrophobic cellulosic materials or compounds (e.g., cellulose acetate phthalate, hydroxypropylmethylcellulose phthalate), polyvinyl acetate polymers (e.g., polyvinyl acetate phthalate), polymers or copolymers derived from acrylic and/or methacrylic acid esters, zein, waxes (alone or in admixture with fatty alcohols), shellac, hydrogenated vegetable oils, and mixtures of two or more thereof. In one embodiment, the hydrophobic polymer is methyl cellulose, ethyl cellulose, propyl cellulose or a mixture of two or more thereof. In another embodiment, the hydrophobic polymer is ethyl cellulose. The compositions of the invention can be coated with a water insoluble compound to a weight gain from about 1 to about 20% by weight.

The sustained release coating can further comprise at least one plasticizer such as triethyl citrate, dibutyl phthalate, propylene glycol, polyethylene glycol, or mixtures of two or more thereof.

The sustained release coating can also contain at least one water soluble compound, such as polyvinylpyrrolidones, hydroxypropylmethylcelluloses, or mixtures thereof. The sustained release coating can comprise at least one water soluble compound in an amount from about 1% to about 6% by weight, preferably in an amount of about 3% by weight.

The sustained release coating can be applied to the metformin core by spraying an aqueous dispersion of the water insoluble compound onto the metformin core. The metformin core can be a granulated composition made, for example, by dry or wet granulation of mixed powders of metformin and at least one binding agent; by coating an inert bead with metformin and at least one binding agent; or by spheronizing mixed powders of metformin and at least one spheronizing agent. Exemplary binding agents include hydroxypropylmethylcelluloses. Exemplary spheronizing agents include microcrystalline celluloses. The inner core can be a tablet made by compressing the granules or by compressing a powder comprising metformin.

In other embodiments, the compositions comprising metformin and a sustained release delivery system, as described herein, are coated with a sustained release coating, as described herein. In still other embodiments, the compositions comprising metformin and a sustained release delivery system, as described herein, are coated with a hydrophobic polymer, as described herein. In still other embodiments, the compositions comprising metformin and a sustained release delivery system, as described herein, are coated with an enteric coating. Exemplary enteric coatings include cellulose acetate phthalate, hydroxypropylmethylcellulose phthalate, polyvinylacetate phthalate, methacrylic acid copolymer, shellac, hydroxypropylmethylcellulose succinate, cellulose acetate trimelliate, or a mixture of two or more thereof. In still other embodiments, the compositions comprising metformin and a sustained release delivery system, as described herein, are coated with a hydrophobic polymer, as described herein, and further coated with an enteric coating, as described herein. In any of the embodiments described herein, the compositions comprising metformin and a sustained release delivery system, as described herein, can optionally be coated with a hydrophilic coating which can be applied above or beneath the sustained release film, above or beneath the hydrophobic coating, and/or above or beneath the enteric coating. Exemplary hydrophilic coatings include hydroxypropylmethylcelluloses.

Without intending to be bound by any theory of the invention, upon oral ingestion of the compositions comprising metformin and a sustained release delivery system and contact of the compositions with gastrointestinal fluids, the compositions swell and gel to form a hydrophilic gel matrix from which metformin is released. The swelling of the gel matrix causes a reduction in the bulk density of the composition and provides the buoyancy necessary to allow the gel matrix to float on the stomach contents to provide a slow delivery of metformin. The hydrophilic matrix, the size of which is dependent upon the size of the original formulation, can swell considerably and become obstructed near the opening of the pylorus. Because metformin is dispersed throughout the formulation (and consequently throughout the gel matrix), a constant amount of metformin can be released per unit time in vivo by dispersion or erosion of the outer portions of the hydrophilic gel matrix. This phenomenon is referred to as a zero order release profile or zero order kinetics. The process continues, with the gel matrix remaining buoyant in the stomach, until substantially all of the metformin is released.

Without intending to be bound by any theory of the invention, the chemistry of certain of the components of the sustained release delivery system, such as the hydrophilic compound (e.g., xanthan gum), is such that the components are considered to be self-buffering agents which are substantially insensitive to the solubility of metformin and the pH changes along the length of the gastrointestinal tract. Moreover, the chemistry of the components is believed to be similar to certain known muco-adhesive substances, such as polycarbophil. Muco-adhesive properties are desirable for buccal delivery systems. Thus, it may be possible that the compositions could potentially loosely interact with the mucin in the gastrointestinal tract and thereby provide another mode by which a constant rate of delivery of metformin is achieved.

The two phenomenon discussed above (hydrophilic gel matrix and muco-adhesive properties) are possible mechanisms by which the compositions of the invention could interact with the mucin and fluids of the gastrointestinal tract and provide a constant rate of delivery of metformin.

The invention provides methods for treating diabetes mellitus by administering to a patient a therapeutically effective amount of the compositions comprising metformin and a sustained release delivery system. In one embodiment, the diabetes mellitus is Type II diabetes mellitus. In another embodiment, the invention provides methods for treating hyperglycemia by administering to a patient a therapeutically effective amount of the compositions comprising metformin and a sustained release delivery system. In another embodiment, the invention provides methods for treating insulin resistance by administering to a patient a therapeutically effective amount of the compositions comprising metformin and a sustained release delivery system. In another embodiment, the invention provides methods for treating precursor syndromes of diabetes mellitus by administering to a patient a therapeutically effective amount of the compositions comprising metformin and a sustained release delivery system.

"Sustained release" means that metformin is released from the composition at a controlled rate so that therapeutically beneficial blood levels of metformin are maintained over an extended period of time, e.g., 1 to 24 hours; 8 to 24 hours; 12 to 24 hours. The metformin sustained release oral solid dosage formulations of the invention can be administered once or twice daily, preferably once daily. The patient can be an animal, preferably a mammal, more preferably a human.

The invention provides pharmaceutical kits comprising one or more containers filled with one or more of the compositions of the invention. The kits can comprise other pharmaceutical compounds known in the art to be therapeutically effective against diabetes, and instructions for use.

EXAMPLES

The following examples are for purposes of illustration only and are not intended to limit the scope of the appended claims.

Example 1

A sustained release delivery system of the invention was prepared as shown in Table 1.

TABLE 1

| Ingredient | % by weight |
| --- | --- |
| Locust bean gum, FCC | 25 |
| Xanthan gum, NF | 25 |
| Dextrose, USP | 35 |
| Calcium Sulfate dihydrate, NF | 10 |
| Ethylcellulose | 5 |
| Alcohol, SD3A, anhydrous | * |
| Total | 100 |

*Removed during processing

An 80 kilo batch of locust bean gum, xanthan gum, dextrose, and calcium sulfate dihydrate were charged in a Fielder Granulator/Mixer (PMA 300) and mixed for 3 minutes.

An ethylcellulose slurry was prepared by placing a 16 kilo batch of anhydrous alcohol in a Coulter Kettle and warming the alcohol to 40° C. to 60° C. While stirring with a Lightnin Mixer, a 4 kilo batch of ethylcellulose was added to the warm alcohol and mixed for at least 5 minutes.

The mixture of locust bean gum, xanthan gum, dextrose and calcium dihydrate was then mixed with the ethylcellulose slurry for 3 minutes at speed I in a PMA300 Mixer, followed by mixing at 1 minute at speed II in a Lightnin Mixer, to produce a granulate. The resulting granulate was put in a Fluid Bed Drier (Calmic) to an LOD of 3–5%. The dried granules were then milled in a Fluid Air Granumill using a 1.00 mm screen at 800 rpm impeller speed.

The resulting granules of the sustained release delivery system comprised 25% by weight locust bean gum; 25% by weight xanthan gum; 35% by weight dextrose; 10% by weight calcium sulfate dihydrate; and 5% by weight ethylcellulose.

Example 2

A sustained release composition comprising 500 mg metformin was prepared as shown in Table 2.

TABLE 2

| Ingredient | Example 2 | Example 3 | Example 4 | Example 5 | Example 6 |
| --- | --- | --- | --- | --- | --- |
| Metformin HCl | 500 | 500 | 500 | 500 | 500 |
| sustained release delivery system | 300 | 500 | 700 | 900 | 500 |
| Silicon dioxide, NF (Syloid 244FP) | 0 | 10 | 0 | 14 | 10 |
| Sodium stearyl fumarate, NF | 8 | 10 | 12 | 14 | 10 |
| OPADRY II ® Clear | 0 | 0 | 0 | 0 | 15.3 |
| SURELEASE ® E-7-7050 | 0 | 0 | 0 | 0 | 35.7 |
| Total Wt. (mg/tablet) | 808 | 1020 | 1212 | 1428 | 1071 |
| % by weight sustained release delivery system | 37 | 49 | 57.8 | 63 | 46.7 |
| % by weight Gum | 18.6 | 24.5 | 28.9 | 31.5 | 23.3 |
| Weight Ratio Drug:Gum | 1:0.3 | 1:0.5 | 1:0.7 | 1:0.9 | 1:0.5 |

500 mg Metformin HCl was passed through a No. 20 screen. The metformin HCl, water, and 300 mg of the sustained release delivery system from Example 1 were charged in a high shear granulator (PP1) to produce a granulated mixture of the sustained release delivery system and metformin HCl. Water was added as needed to produce consistent granules. The resulting granules were dried in a Fluid Bed Drier (Niro Aeromatic Strea 1) and then milled with a FizMill using screen #1521-0050.

8 mg sodium stearyl fumarate was dry blended using a Patterson Kelly Blendmaster V-blender to produce milled granules.

The sodium stearyl fumarate granules were compress blended with the metformin HCl/sustained release delivery system granules into tablets with a Korsh table press using 0.374×0.748 inch modified oval shaped punches.

The resulting sustained release tablet weighed 808 mg; contained the sustained release delivery system in an amount of 37% by weight, contained 18.6% gum (i.e., locust bean gum plus xanthan gum), and the ratio of metformin HCl to gum (i.e., locust bean gum plus xanthan gum) was 1:0.3.

Example 3

A sustained release composition comprising 500 mg metformin was prepared as shown in Table 2.

500 mg Metformin HCl was passed through a No. 20 screen. The metformin HCl, water, and 500 mg of the sustained release delivery system from Example 1 were charged in a high shear granulator (PP1) to produce a granulated mixture of the sustained release delivery system and metformin HCl. Water was added as needed to produce consistent granules. The resulting granules were dried in a Fluid Bed Drier (Niro Aeromatic Strea 1) and then milled with a FizMill using screen #1521-0050.

10 mg silicon dioxide and 10 mg sodium stearyl fumarate were dry blended using a Patterson Kelly Blendmaster V-blender to produce milled granules.

The silicon dioxide/sodium stearyl fumarate granules were compress blended with the metformin HCl/sustained release delivery system granules into tablets with a Korsh table press using 0.374×0.748 inch modified oval shaped punches.

The resulting sustained release tablet weighed 1020 mg; contained the sustained release delivery system in an amount of 49% by weight, contained 24.5% gum (i.e., locust bean gum plus xanthan gum), and the ratio of metformin HCl to gum (i.e., locust bean gum plus xanthan gum) was 1:0.5.

Example 4

A sustained release composition comprising 500 mg metformin was prepared as shown in Table 2.

500 mg Metformin HCl was passed through a No. 20 screen. The metformin HCl, water, and 700 mg of the sustained release delivery system from Example 1 were charged in a high shear granulator (PP1) to produce a granulated mixture of the sustained release delivery system and metformin HCl. Water was added as needed to produce consistent granules. The resulting granules were dried in a Fluid Bed Drier (Niro Aeromatic Strea 1) and then milled with a FizMill using screen #1521-0050.

12 mg sodium stearyl fumarate was dry blended using a Patterson Kelly Blendmaster V-blender to produce milled granules.

The sodium stearyl fumarate granules were compress blended with the metformin HCl/sustained release delivery system granules into tablets with a Korsh table press using 0.374×0.748 inch modified oval shaped punches.

The resulting sustained release tablet weighed 1212 mg; contained the sustained release delivery system in an amount of 57.8% by weight, contained 28.9% gum (i.e., locust bean gum plus xanthan gum), and the ratio of metformin HCl to gum (i.e., locust bean gum plus xanthan gum) was 1:0.7.

Example 5

A sustained release composition comprising 500 mg metformin was prepared as shown in Table 2.

500 mg Metformin HCl was passed through a No. 20 screen. The metformin HCl, water, and 900 mg of the sustained release delivery system from Example 1 were charged in a high shear granulator (PP1) to produce a granulated mixture of the sustained release delivery system and metformin HCl. Water was added as needed to produce consistent granules. The resulting granules were dried in a Fluid Bed Drier (Niro Aeromatic Strea 1) and then milled with a FizMill using screen #1521-0050.

14 mg silicon dioxide and 14 mg sodium stearyl fumarate was dry blended using a Patterson Kelly Blendmaster V-blender to produce milled granules.

The silicon dioxide/sodium stearyl fumarate granules were compress blended with the metformin HCl/sustained release delivery system granules into tablets with a Korsh table press using 0.374×0.748 inch modified oval shaped punches.

The resulting sustained release tablet weighed 1428 mg; contained the sustained release delivery system in an amount of 63% by weight, contained 31.5% gum (i.e., locust bean gum plus xanthan gum), and the ratio of metformin HCl to gum (i.e., locust bean gum plus xanthan gum) was 1:0.9.

Example 6

A sustained release composition comprising 500 mg metformin was prepared as shown in Table 2.

500 mg Metformin HCl was passed through a No. 20 screen. The metformin HCl, water, and 500 mg of the sustained release delivery system from Example 1 were charged in a high shear granulator (PP1) to produce a granulated mixture of the sustained release delivery system and metformin HCl. Water was added as needed to produce consistent granules. The resulting granules were dried in a Fluid Bed Drier (Niro Aeromatic Strea 1) and then milled with a FizMill using screen #1521-0050.

10 mg silicon dioxide and 10 mg sodium stearyl fumarate was dry blended using a Patterson Kelly Blendmaster V-blender to produce milled granules.

The silicon dioxide/sodium stearyl fumarate granules were compress blended with the metformin HCl/sustained release delivery system granules into tablets with a Korsh table press using 0.374×0.748 inch modified oval shaped punches.

The sustained release tablet was then coated with a SURELEASE®:OPADRY II® coating in a ratio of 70:30, which was prepared by dispersing the OPADRY II® in purified water with stirring until a solution was formed. SURELEASE® was mixed with an appropriate amount of purified water to achieve the desired solids content until a uniform suspension was obtained. The solution and suspension were mixed thoroughly together.

SURELEASE® and OPADRY II® are commercially available from Colorcon, West Point, Pa. SURELEASE® is a plasticized aqueous ethylcellulose dispersion. OPADRY II® comprises polymer, polysaccharide and pigment.

The sustained release tablets were spray coated using Vector LDCS 20/30 to a weight gain of 5%. The coated tablets were allowed to dry and cool at room temperature.

The resulting sustained release tablet weighed 1071 mg; contained the sustained release delivery system in an amount of 46.7% by weight, contained 23.3% gum (i.e., locust bean gum plus xanthan gum), and the ratio of metformin HCl to gum (i.e., locust bean gum plus xanthan gum) was 1:0.5.

Example 7

A sustained release delivery system of the invention was prepared as shown in Table 3.

TABLE 3

| Ingredient | % by weight |
| --- | --- |
| Locust bean gum, FCC | 30 |
| Xanthan gum, NF | 20 |
| Mannitol, USP | 40 |
| Calcium Sulfate dihydrate, NF | 10 |
| Purified water | * |
| Total | 100 |

*Removed during processing

A 1 kilo batch of locust bean gum, xanthan gum, mannitol, and calcium sulfate dihydrate was charged in an Aeromatic-Fielder PP1 granulator and mixed to form granules. The resulting granules were mixed with water to achieve consistent granules. The granules were then dried in a Fluid Bed Drier (Niro Aeromatic Strea 1), and subsequently milled with a FizMill using screen #1521-0033.

The resulting granules of the sustained release delivery system comprised 30% by weight locust bean gum; 20% by weight xanthan gum; 40% by weight mannitol; and 10% by weight calcium sulfate dihydrate.

Example 8

A sustained release composition comprising 500 mg metformin was prepared as shown in Table 4.

TABLE 4

| Ingredient | Example 8 | Example 9 | Example 10 |
| --- | --- | --- | --- |
| Metformin HCl | 500 | 500 | 500 |
| sustained release delivery system | 500 | 500 | 500 |
| Silicon dioxide, NF (Syloid 244FP) | 10 | 10 | 10 |
| Sodium stearyl fumarate, NF | 10 | 10 | 10 |
| OPADRY II ® Clear | 0 | 6.1 | 10.2 |
| SURELEASE ® E-7-7050 | 0 | 24.5 | 40.8 |
| Water | * | * | * |
| Total Wt. (mg/tablet) | 1020 | 1050.6 | 1071 |
| % by weight sustained release delivery system | 49 | 47.6 | 46.7 |
| % by weight Gum | 24.5 | 23.8 | 23.3 |
| Weight Ratio Drug:Gum | 1:0.5 | 1:0.5 | 1:0.5 |

*Removed during processing 500 mg Metformin HCl was passed through a No. 20 screen. The metformin HCl, water, and 500 mg of the sustained release delivery system from Example 7 were charged in a high shear granulator (PP1) to produce a granulated mixture of the sustained release delivery system and metformin HCl. Water was added as needed to produce consistent granules. The resulting granules were dried in a Fluid Bed Drier (Niro Aeromatic Strea 1) and then milled with a FizMill using screen #1521-0050.

10 mg silicon dioxide and 10 mg sodium stearyl fumarate were dry blended using a Patterson Kelly Blendmaster V-blender to produce milled granules.

The silicon dioxide/sodium stearyl fumarate granules were compressed blended with the metformin HCl/sustained release delivery system granules into tablets with a Korsh table press using 0.374×0.748 inch modified oval shaped punches.

The resulting sustained release tablet weighed 1020 mg; contained the sustained release delivery system in an amount of 49% by weight, contained 24.5% gum (i.e., locust bean gum plus xanthan gum), and the ratio of metformin HCl to gum (i.e., locust bean gum plus xanthan gum) was 1:0.5.

Example 9

A sustained release composition comprising 500 mg metformin was prepared as shown in Table 4.

500 mg Metformin HCl was passed through a No. 20 screen. The metformin HCl, water, and 500 mg of the sustained release delivery system from Example 7 were charged in a high shear granulator (PP1) to produce a granulated mixture of the sustained release delivery system and metformin HCl. Water was added as needed to produce consistent granules. The resulting granules were dried in a Fluid Bed Drier (Niro Aeromatic Strea 1) and then milled with a FizMill using screen #1521-0050.

10 mg silicon dioxide and 10 mg sodium stearyl fumarate were dry blended using a Patterson Kelly Blendmaster V-blender to produce milled granules.

The silicon dioxide/sodium stearyl fumarate granules were compressed blended with the metformin HCl/sustained release delivery system granules into tablets with a Korsh table press using 0.374×0.748 inch modified oval shaped punches.

The sustained release tablet was then coated with a SURELEASE®:OPADRY II® coating in a ratio of 80:20 (i.e., 24.5 grams SURELEASE® and 6.1 grams OPADRY II® clear), which was prepared by dispersing the OPADRY II® in purified water with stirring until a solution was formed. SURELEASE® was mixed with an appropriate amount of purified water to achieve the desired solids content until a uniform suspension was obtained. The solution and suspension were mixed thoroughly together.

SURELEASE® is a plasticized aqueous ethylcellulose dispersion. OPADRY II® is a combination of polymer, polysaccharide and pigment.

The sustained release tablets were spray coated using Vector LDCS 20/30 to a weight gain of 3%. The coated tablets were allowed to dry and cool at room temperature.

The resulting sustained release tablet weighed 1050.6 mg; contained the sustained release delivery system in an amount of 47.6% by weight, contained 23.8% gum (i.e., locust bean gum plus xanthan gum), and the ratio of metformin HCl to gum (i.e., locust bean gum plus xanthan gum) was 1:0.5.

Example 10

A sustained release composition comprising 500 mg metformin was prepared as shown in Table 4.

500 mg Metformin HCl was passed through a No. 20 screen. The metformin HCl, water, and 500 mg of the sustained release delivery system from Example 7 were charged in a high shear granulator (PP1) to produce a granulated mixture of the sustained release delivery system and metformin HCl. Water was added as needed to produce consistent granules. The resulting granules were dried in a Fluid Bed Drier (Niro Aeromatic Strea 1) and then milled with a FizMill using screen #1521-0050.

10 mg silicon dioxide and 10 mg sodium stearyl fumarate were dry blended using a Patterson Kelly Blendmaster V-blender to produce milled granules.

The silicon dioxide/sodium stearyl fumarate granules were compressed blended with the metformin HCl/sustained release delivery system granules into tablets with a Korsh table press using 0.374×0.748 inch modified oval shaped punches.

The sustained release tablet was then coated with a SURELEASE®:OPADRY II® coating in a ratio of 80:20 (i.e., 40.8 mg SURELEASE® and 10.2 mg OPADRY II® clear), which was prepared by dispersing the OPADRY II® in purified water with stirring until a solution was formed. SURELEASE® was mixed with an appropriate amount of purified water to achieve the desired solids content until a uniform suspension was obtained. The solution and suspension were mixed thoroughly together.

The sustained release tablets were spray coated using Vector LDCS 20/30 to a weight gain of 5%. The coated tablets were allowed to dry and cool at room temperature.

The resulting sustained release tablet weighed 1071 mg; contained the sustained release delivery system in an amount of 46.7% by weight, contained 23.3% gum (i.e., locust bean gum plus xanthan gum), and the ratio of metformin HCl to gum (i.e., locust bean gum plus xanthan gum) was 1:0.5.

Example 11

A sustained release delivery system of the invention was prepared as shown in Table 5.

TABLE 5

| Ingredient | % by weight |
| --- | --- |
| Locust bean gum, FCC | 42 |
| Xanthan gum, NF | 28 |
| Mannitol, USP | 20 |
| Calcium Sulfate dihydrate, NF | 10 |
| Purified water | * |
| Total | 100 |

*Removed during processing.

A 1 kilo batch of locust bean gum, xanthan gum, mannitol, and calcium sulfate dihydrate was charged in an Aeromatic-Fielder PP1 granulator and mixed to form granules. The resulting granules were mixed with water to achieve consistent granules. The granules were then dried in a Fluid Bed Drier (Niro Aeromatic Strea 1), and subsequently milled with a FizMill using screen #1521-0033.

The resulting granules of the sustained release delivery system comprised 42% by weight locust bean gum; 28% by weight xanthan gum; 20% by weight mannitol; and 10% by weight calcium sulfate dihydrate.

Example 12

A sustained release composition comprising 500 mg metformin was prepared as shown in Table 6.

TABLE 6

| Ingredient | Example 12 |
| --- | --- |
| Metformin HCl | 500 |
| sustained release delivery system | 500 |
| Silicon dioxide, NF (Syloid 244FP) | 10 |
| Sodium stearyl fumarate, NF | 10 |
| Total Wt. (mg/tablet) | 1020 |
| % by weight sustained release delivery system | 49 |
| % by weight Gum | 34.3 |
| Weight Ratio Drug:Gum | 1:0.7 |

500 mg Metformin HCl was passed through a No. 20 screen. The metformin HCl, water, and 500 mg of the sustained release delivery system from Example 11 were charged in a high shear granulator (PP1) to produce a granulated mixture of the sustained release delivery system and metformin HCl. Water was added as needed to produce consistent granules. The resulting granules were dried in a Fluid Bed Drier (Niro Aeromatic Strea 1) and then milled with a FizMill using screen #1521-0050.

10 mg silicon dioxide and 10 mg sodium stearyl fumarate were dry blended using a Patterson Kelly Blendmaster V-blender to produce milled granules.

The silicon dioxide/sodium stearyl fumarate granules were compressed blended with the metformin HCl/sustained release delivery system granules into tablets with a Korsh table press using 0.374×0.748 inch modified oval shaped punches.

The resulting sustained release tablet weighed 1020 mg; contained the sustained release delivery system in an amount of 49% by weight, contained 34.3% gum (i.e., locust bean gum plus xanthan gum), and the ratio of metformin HCl to gum (i.e., locust bean gum plus xanthan gum) was 1:0.7.

Example 13

A sustained release composition comprising 500 mg metformin was prepared as shown in Table 7.

TABLE 7

| Ingredient | Example 13 | Example 14 | Example 15 |
| --- | --- | --- | --- |
| Metformin HCl | 500 | 500 | 500 |
| sustained release delivery system | 700 | 400 | 700 |
| Hydoxypropyl methylcellulose (Methocel E5LV) | 60 | 45 | 60 |
| Silicon dioxide (Syloid 244FP) | 6 | 5 | 6 |
| Sodium stearyl fumarate, NF | 12 | 9 | 12 |
| SURELEASE ® E-7-7050 | N/A | N/A | 44.7 |
| OPADRY ® II Clear | N/A | N/A | 19.2 |
| Water | * | * | * |
| Total Wt. (mg/tablet) | 1278 | 959 | 1341.9 |
| % by weight sustained release delivery system | 54.8 | 41.7 | 52.2 |
| % by weight Gum | 38.3 | 29.2 | 36.5 |
| Weight Ratio Drug:Gum | 1:0.98 | 1:0.56 | 1:0.98 |

*Removed During Processing 500 mg Metformin HCl was passed through a No. 20 screen.

A hydroxypropyl methylcellulose suspension was prepared by adding 60 mg hydroxypropyl methylcellulose to water while stirring.

The metformin HCl and 700 mg of the sustained release delivery system from Example 11, and the hydroxypropyl methylcellulose suspension were charged in a high shear granulator (PMA 25) to produce a granulated mixture. Water was added as needed to produce consistent granules. The resulting granules were dried in a Fluid Bed Drier (MP-1) and then milled with a FizMill using screen #1521-0050.

The resulting granules, 6 mg silicon dioxide, and 12 mg sodium stearyl fumarate were dry blended using a Patterson Kelly Blendmaster V-blender to produce milled granules.

The resulting milled granules were compressed into tablets using a Cadmach press using 0.374×0.748 inch modified oval shaped punches.

The resulting sustained release tablet weighed 1278 mg; contained the sustained release delivery system in an amount of 54.8% by weight, contained 38.3% gum (i.e., locust bean gum plus xanthan gum), and the ratio of metformin HCl to gum (i.e., locust bean gum plus xanthan gum) was 1:0.98.

Example 14

A sustained release composition comprising 500 mg metformin was prepared as shown in Table 7.

500 mg Metformin HCl was passed through a No. 20 screen.

A hydroxypropyl methylcellulose suspension was prepared by adding 45 mg hydroxypropyl methylcellulose to water while stirring.

The metformin HCl and 400 mg of the sustained release delivery system from Example 11, and the hydroxypropyl methylcellulose suspension were charged in a high shear granulator (PMA 25) to produce a granulated mixture. Water was added as needed to produce consistent granules. The resulting granules were dried in a Fluid Bed Drier (MP-1) and then milled with a FizMill using screen #1521-0050.

The resulting granules, 5 mg silicon dioxide, and 9 mg sodium stearyl fumarate were dry blended using a Patterson Kelly Blendmaster V-blender to produce milled granules.

The resulting milled granules were compressed into tablets using a Cadmach press using 0.374×0.748 inch modified oval shaped punches.

The resulting sustained release tablet weighed 959 mg; contained the sustained release delivery system in an amount of 41.7% by weight, contained 29.2% gum (i.e., locust bean gum plus xanthan gum), and the ratio of metformin HCl to gum (i.e., locust bean gum plus xanthan gum) was 1:0.56.

Example 15

A sustained release composition comprising 500 mg metformin was prepared as shown in Table 7.

500 mg Metformin HCl was passed through a No. 20 screen.

A hydroxypropyl methylcellulose suspension was prepared by adding 60 mg hydroxypropyl methylcellulose to water while stirring.

The metformin HCl and 700 mg of the sustained release delivery system from Example 11, and the hydroxypropyl methylcellulose suspension were charged in a high shear granulator (PMA 25) to produce a granulated mixture. Water was added as needed to produce consistent granules. The resulting granules were dried in a Fluid Bed Drier (MP-1) and then milled with a FizMill using screen #1521-0050.

The resulting granules, 6 mg silicon dioxide, and 12 mg sodium stearyl fumarate were dry blended using a Patterson Kelly Blendmaster V-blender to produce milled granules.

The resulting milled granules were compressed into tablets using a Cadmach press using 0.374×0.748 inch modified oval shaped punches.

The sustained release tablet was then coated with a SURELEASE®:OPADRY II® coating in a ratio of 70:30 (i.e., 44.7 mg SURELEASE® and 19.2 mg OPADRY II® clear), which was prepared by dispersing the OPADRY II® in purified water with stirring until a solution was formed. SURELEASE® was mixed with an appropriate amount of purified water to achieve the desired solids content until a uniform suspension was obtained. The solution and suspension were mixed thoroughly together.

The sustained release tablets were spray coated using Vector LDCS 20/30 to a weight gain of 5%. The coated tablets were allowed to dry and cool at room temperature.

The resulting sustained release tablet weighed 1341.9 mg; contained the sustained release delivery system in an amount of 52.2% by weight, contained 36.5% gum (i.e., locust bean gum plus xanthan gum), and the ratio of metformin HCl to gum (i.e., locust bean gum plus xanthan gum) was 1:0.98.

Example 16

A dissolution study was performed to evaluate the effect of drug:gum ratio on the drug release profile of various metformin formulations. A comparison was performed among tablets prepared as described in Example 2 (19% gum), Example 3 (25% gum), Example 4 (29% gum), and Example 5 (32% gum). The tablets were dissolved using a USP miI apparatus in 250 ml of media at pH 6.8 (sodium phosphate monobasic/NaOH). Dissolution was performed at 37° C. with 15 dpm agitation. Percent dissolution measurements were taken at 0, 1, 2, 4, 8, 12, and 16 hour time points.

Figure 1:
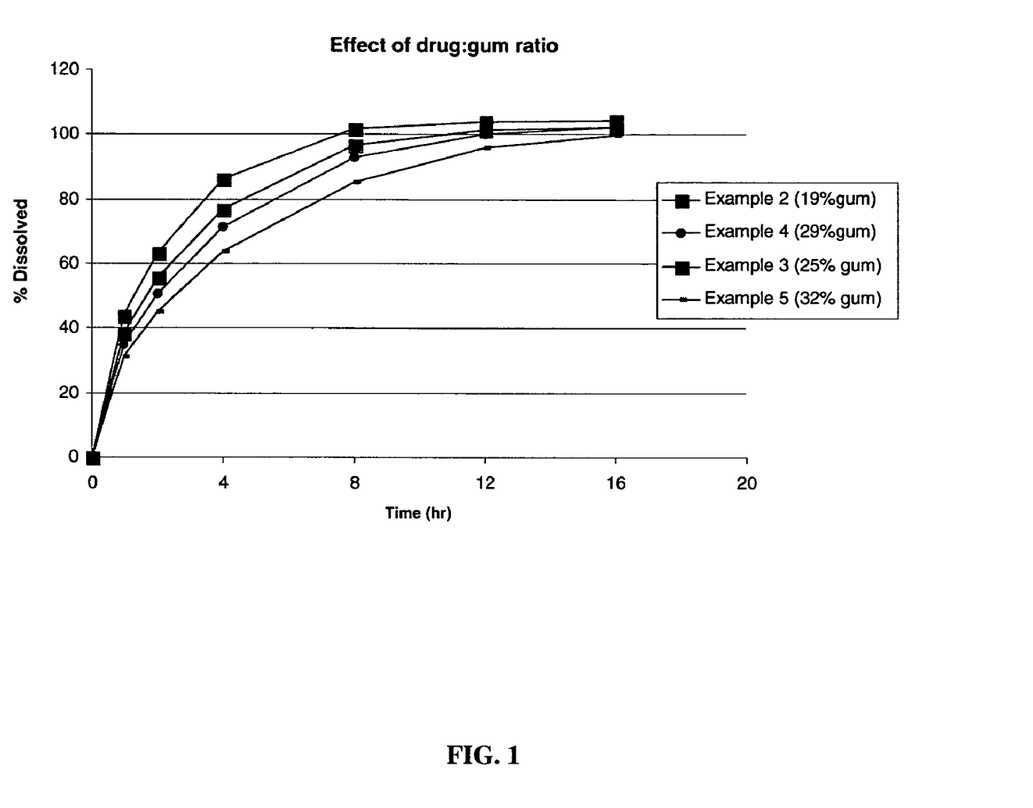
FIG. 1 is a graphic representation of the in vitro dissolution profile of Metformin HCl tablets according to certain embodiments of the invention, illustrating the effect of drug:gum ratio on dissolution time.

Table 8 and FIG. 1 show the dissolution results, which indicate that increasing the drug:gum ratio decreases the drug release rate.

TABLE 8

| Time (hr) | Example 2 | Example 3 | Example 4 | Example 5 |
| --- | --- | --- | --- | --- |
| 0 | 0 | 0 | 0 | 0 |
| 0.97 | 44 | 38.5 | 34.9 | 31.2 |
| 2 | 63.4 | 55.6 | 50.7 | 45.3 |
| 4 | 86.3 | 77 | 71.2 | 63.6 |
| 8 | 101.8 | 96.9 | 93 | 85.2 |
| 12 | 103.9 | 101.5 | 100.3 | 96.1 |
| 16 | 104.3 | 102.2 | 102.4 | 99.8 |
| Remnants | 0 | 0.3 | 0.8 | 1.4 |
| % Recovery | 104.3 | 102.5 | 103.2 | 101.2 |

Example 17

A dissolution study was performed to evaluate the effect of the percentage of gum in the sustained release delivery system on the drug release profile of metformin formulations. Tablets prepared as described in Example 3 with the sustained release delivery system of Example 1 (50% gum in sustained release delivery system) were compared to tablets prepared as described in Example 12 with the sustained release delivery system of Example 11 (70% gum in sustained release delivery system). Dissolution was performed as described in Example 16.

Figure 2:
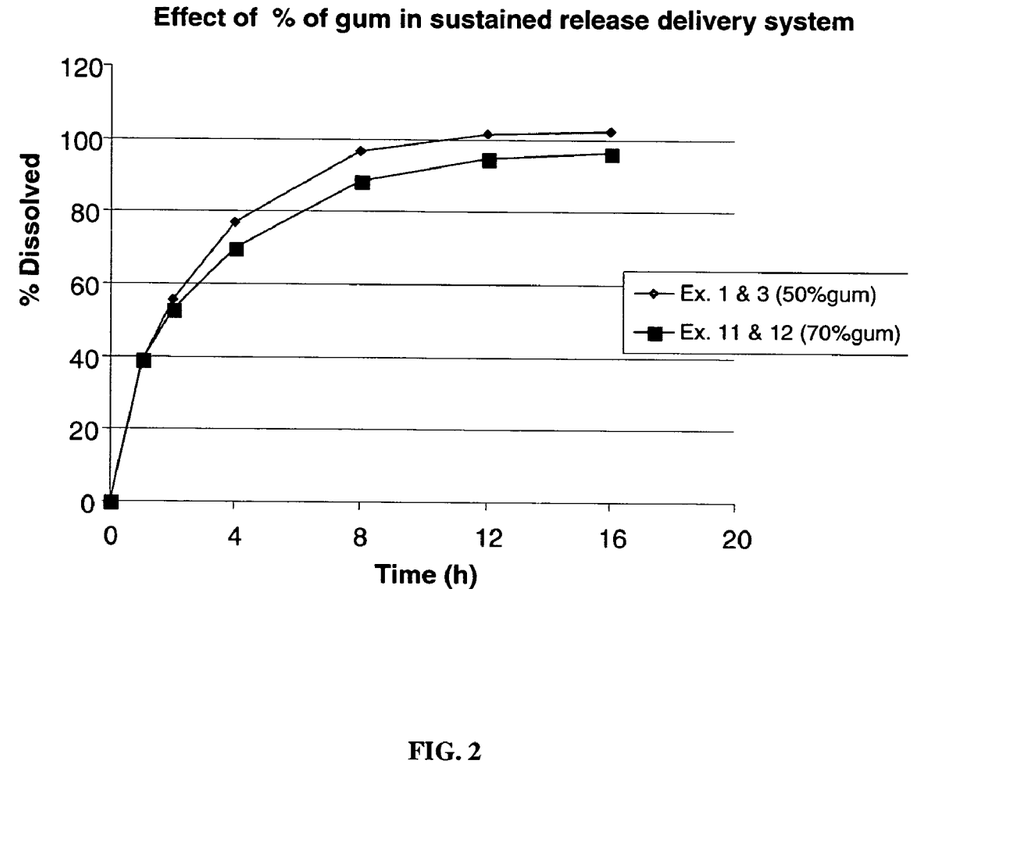
FIG. 2 is a graphic representation of the in vitro dissolution profile of Metformin HCl tablets according to certain embodiments of the invention, illustrating the effect of percent gum in the sustained release delivery system on dissolution time.

Table 9 and FIG. 2 show the dissolution results, which indicate that increasing the percentage of gum in the sustained release delivery system decreases the drug release rate.

TABLE 9

| Time (hr) | Examples 1 & 3 | Examples 11 & 12 |
|---|---|---|
| 0 | 0 | 0 |
| 1 | 38.5 | 39.2 |
| 2 | 55.6 | 52.7 |
| 4 | 77 | 70 |
| 8 | 96.9 | 88.5 |
| 12 | 101.5 | 94.8 |
| 16 | 102.2 | 96.2 |
| Remnants | 0.3 | 0.1 |
| % Recovery | 102.5 | 96.3 |

Example 18

A dissolution study was performed to evaluate the effect that the ratio of SURELEASE® to OPADRY II® in the coating has on the drug release profile of coated metformin formulations. A comparison was performed between tablets prepared as described in Example 6 (70:30 SURELEASE®: OPADRY II®) and Example 10 (80:20 SURELEASE®: OPADRY II®), both of which had same weight gain (5%) due to the coating. Dissolution was performed as described in Example 16.

Figure 3:
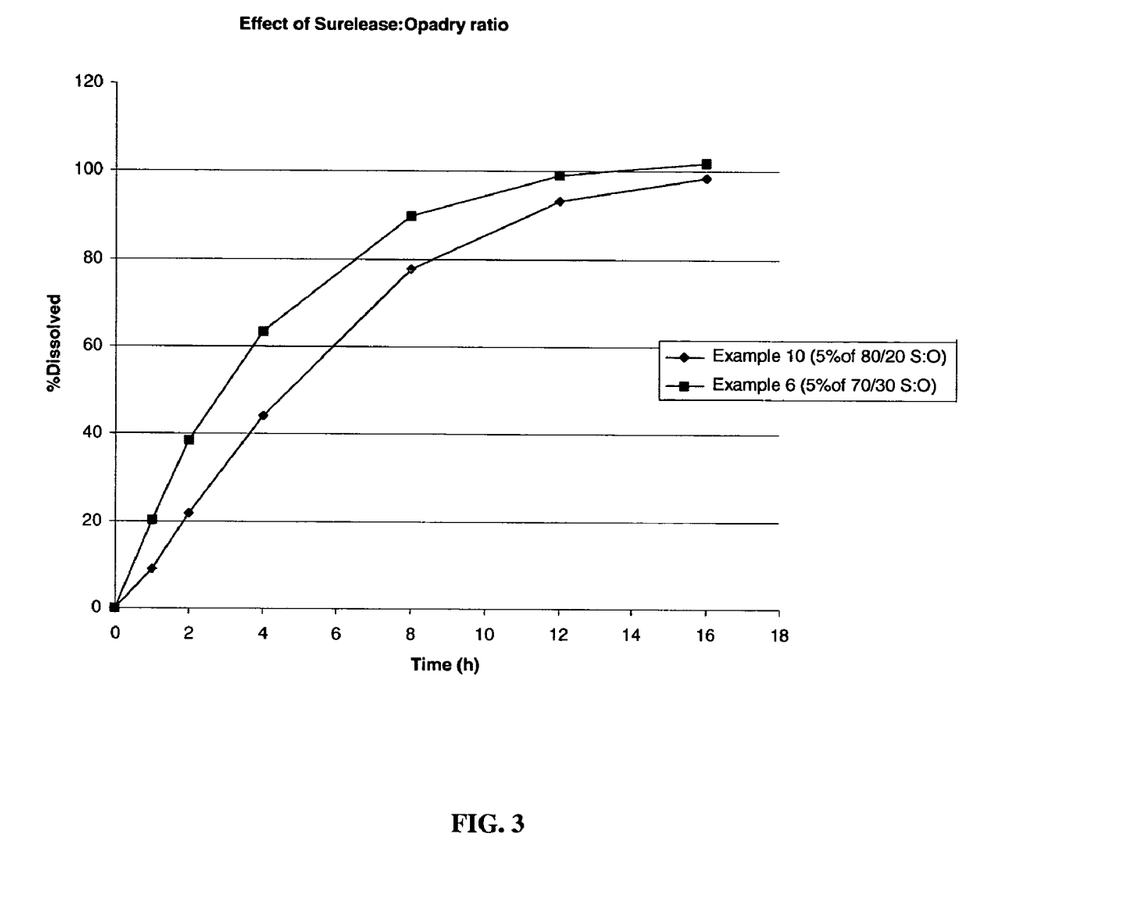
FIG. 3 is a graphic representation of the in vitro dissolution profile of coated Metformin HCl tablets according to certain embodiments of the invention, illustrating the effect of SURELEASE®:OPADRY II® ratio in the coating on dissolution time.

Table 10 and FIG. 3 show the dissolution results, which indicate that increasing the percentage of SURELEASE® for the same weight gain of coating decreases the drug release rate.

TABLE 10

| Time (hr) | Example 10 | Example 6 |
|---|---|---|
| 0 | 0 | 0 |
| 1 | 9.1 | 20.2 |
| 2 | 21.8 | 38.4 |
| 4 | 44.2 | 63.3 |
| 8 | 77.6 | 90 |
| 12 | 93.3 | 99.3 |
| 16 | 98.7 | 102 |
| Remnants | 1.9 | 0.6 |
| % Recovery | 100.5 | 102.6 |

Example 19

A dissolution study was performed to evaluate the effect on drug release profile of coating weight gain for a constant SURELEASE®:OPADRY II® ratio in the coating. A comparison was performed between tablets prepared as described in Example 9 (3% weight gain of coating) and Example 10 (5% weight gain of coating). Dissolution was performed as described in Example 16.

Figure 4:
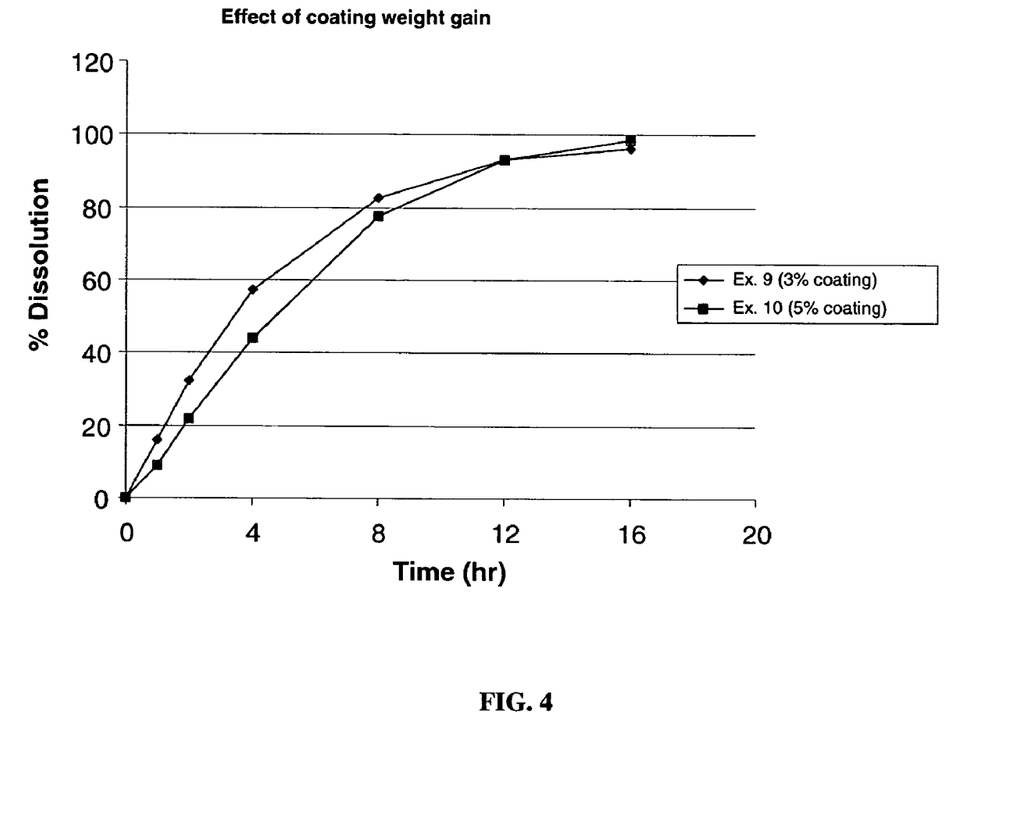
FIG. 4 is a graphic representation of the in vitro dissolution profile of coated Metformin HCl tablets according to certain embodiments of the invention, illustrating the effect of coating weight gain on dissolution time.

Table 11 and FIG. 4 show the dissolution results, which indicate that increasing the weight gain of coating decreases the drug release rate.

TABLE 11

| Time (hr) | Example 9 | Example 10 |
|---|---|---|
| 0 | 0 | 0 |
| 1 | 16.1 | 9.1 |
| 2 | 32.4 | 21.8 |
| 4 | 57.1 | 44.2 |
| 8 | 82.7 | 77.6 |
| 12 | 93.2 | 93.3 |
| 16 | 96.1 | 98.7 |
| Remnants | 0.8 | 1.9 |
| % Recovery | 96.9 | 100.5 |

Example 20

A dissolution study was performed to compare the drug release profiles of metformin tablets prepared as described in Example 13 (700 mg sustained release delivery system), Example 14 (400 mg sustained release delivery system), and Example 15 (coated to 5% weight gain). Dissolution was performed as described in Example 16.

Figure 5:
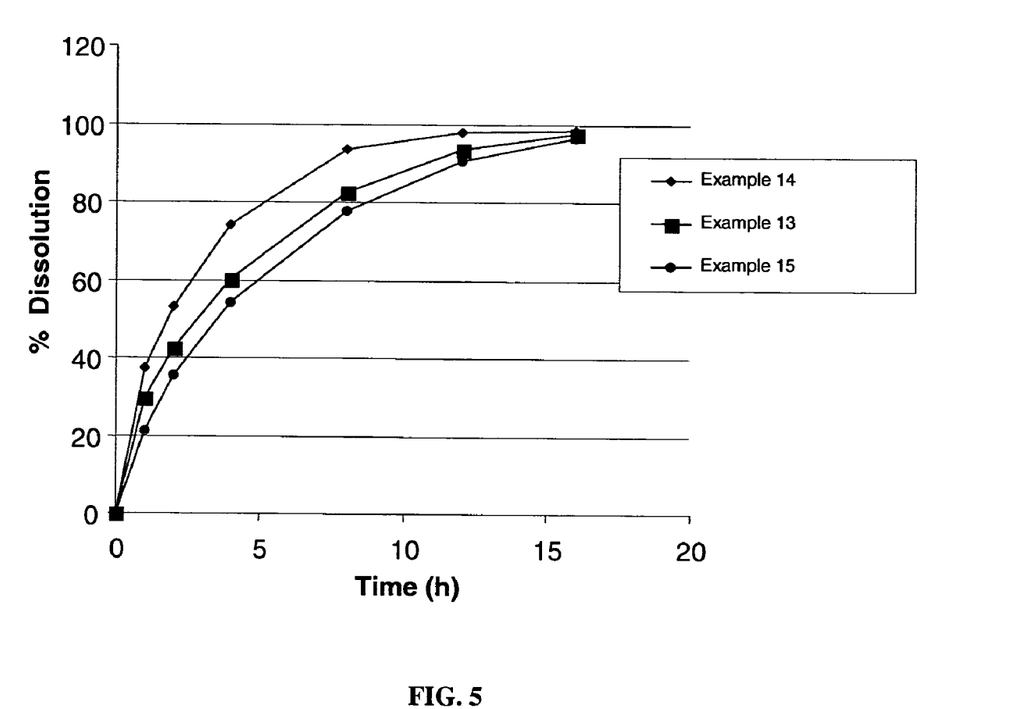
FIG. 5 is a graphic representation of the in vitro dissolution profile of Metformin HCl tablets according to certain embodiments of the invention, illustrating the effect of coating and quantity of sustained release delivery system on dissolution time.

Table 12 and FIG. 5 show the dissolution results, which indicate that drug release rate is slower for the formulation containing more of the sustained release delivery system (Example 13), and for the coated formulation (Example 15).

TABLE 12

| Time (hr) | Example 14 | Example 13 | Example 15 |
|---|---|---|---|
| 0 | 0 | 0 | 0 |
| 1 | 37.5 | 29.9 | 21.4 |
| 2 | 53.3 | 42.6 | 35.5 |
| 4 | 74.1 | 60.3 | 54.3 |
| 8 | 93.4 | 82.7 | 77.9 |
| 12 | 98 | 93.7 | 90.5 |
| 16 | 98.3 | 97.7 | 96.5 |
| Remnants | 0 | 0.8 | 3.3 |
| % Recovery | 98.3 | 98.5 | 99.1 |

Example 21

A Phase I, randomized, analytical blind, four-way crossover study was conducted to compare the oral bioavailability of single doses of 500 mg Metformin HCl extended release formulations prepared as described in Examples 13, 14, and 15 to the oral bioavailability of a single dose of Glucophage XR 500 mg tablets (Bristol-Myers Squibb Co., Princeton, N.J.). A fasted and fed (following a standard breakfast) study was performed on 12 healthy volunteers. Table 13 describes the results obtained from the blood plasma analysis.

TABLE 13

|  |  | Example 13 | Example 14 | Example 15 | Glucophage SR |
|---|---|---|---|---|---|
| $C_{max}$[1] (ng/mL) | | | | | |
| Fast | GM* | 579.84 | 665.17 | 442.90 | 609.48 |
|  | Range | 258.45–912.37 | 416.96–1480.13 | 220.68–720.47 | 354.06–1183.84 |
|  | CV %** | 30.5 | 41.2 | 30.6 | 37.8 |
| Fed | GM* | 697.83 | 833.45 | 608.16 | 646.55 |
|  | Range | (522.86–871.24) | (612.82–1238.35) | (327.82–768.58) | (472.47–818.97) |
|  | CV %** | 16.8 | 21.1 | 21.5 | 17.8 |
| $AUC_{inf}$[2] (ng·h/mL) | | | | | |
| Fast | GM* | 4496.6 | 4885.6 | 3959.9 | 5098.7 |
|  | Range | 2863.5–5972.76 | 2756.5–10437.1 | 2340.3–5115.06 | 2924.3–6626.16 |
|  | CV %** | 24.7 | 45.7 | 22.6 | 25.4 |
| Fed | GM* | 6554.2 | 6328.2 | 5561.2 | 6798.9 |
|  | Range | (4589.3–8054.71) | (4555.2–8351.76) | (3574.6–8814.95) | 4602.7–9112.89 |
|  | CV %** | 16.5 | 19.5 | 28.3 | 20.7 |
| $T_{max}$[3] (h) | | | | | |
| Fast | Median | 3.50 | 3.50 | 4.00 | 4.00 |
|  | Range | 2.00–6.00 | 2.00–5.00 | 2.00–5.00 | 2.00–6.00 |
| Fed | Median | 5.00 | 4.50 | 5.00 | 5.00 |
|  | Range | 4.00–7.00 | 4.00–6.00 | 4.00–8.00 | 4.00–7.00 |

*Geometric Mean
**Coefficient of Variation
[1]Maximum observed post-dose concentration
[2]Area under the concentration-time curve from time zero to infinity
[3]Time to attain $C_{max}$ The patents, patent applications, and publications cited herein are incorporated by reference herein in their entirety.

Various modifications of the invention, in addition to those described herein, will be apparent to one skilled in the art from the foregoing description. Such modifications are intended to fall within the scope of the appended claims.

What is claimed is:

1. A sustained-release pharmaceutical composition comprising metformin or a pharmaceutically acceptable salt thereof in an amount of about 100 mg to about 1000 mg; and a sustained-release delivery system comprising xanthan gum in an amount of about 5% to about 60% by weight; locust bean gum in an amount of about 10% to about 70% by weight; and at least one pharmaceutical diluent selected from the group consisting of monosaccharides, disaccharides, polyhydric alcohols, and mixtures of two or more thereof in an amount of about 5% to about 80% by weight, wherein therapeutically beneficial blood levels of metformin are maintained over a period of time from about 1 to about 24 hours.

2. The sustained-release pharmaceutical composition of claim 1, wherein the metformin or the pharmaceutically acceptable salt thereof is present in an amount of about 300 mg to about 700 mg; and the sustained-release delivery system comprises xanthan gum in an amount of about 20% to about 40% by weight; locust bean gum in an amount of about 20% to about 60% by weight; and the at least one pharmaceutical diluent in an amount of about 10% to about 50% by weight.

3. The sustained-release pharmaceutical composition of claim 1, wherein the metformin or the pharmaceutically acceptable salt thereof is present in an amount of about 500 mg; and the sustained-release delivery system comprises xanthan gum in an amount of about 28% by weight; locust bean gum in an amount of about 42% by weight; and the at least one pharmaceutical diluent in an amount of about 20% by weight.

4. The sustained-release pharmaceutical composition of claim 1, wherein the sustained-release delivery system further comprises calcium sulfate in an amount of about 0.5% to about 30% by weight.

5. The sustained-release pharmaceutical composition of claim 2, wherein the sustained-release delivery system further comprises calcium sulfate in an amount of about 5% to about 20% by weight.

6. The sustained-release pharmaceutical composition of claim 3, wherein the sustained-release delivery system further comprises calcium sulfate in an amount of about 10% by weight.

7. The sustained-release pharmaceutical composition of claim 1, wherein the at least one pharmaceutical diluent is mannitol.

8. The sustained-release pharmaceutical composition of claim 1, wherein the sustained release delivery system further comprises ethylcellulose in an amount of about 2% to about 10% by weight.

9. The sustained-release pharmaceutical composition of claim 1, wherein the sustained-release delivery system further comprises ethylcellulose in an amount of about 3% to about 7% by weight.

10. The sustained-release pharmaceutical composition of claim 1, further comprising a coating on the outside of the pharmaceutical composition, wherein the coating comprises an alkyl cellulose, a hydrophobic cellulosic compound, a polyvinyl acetate polymer, a polymer or copolymer derived from an acrylic acid ester and/or a methacrylic acid ester, a zein, a wax, a shellac, a hydrogenated vegetable oil or a mixture of two or more thereof.

11. The sustained-release pharmaceutical composition of claim 10, wherein the coating comprises ethyl cellulose to a weight gain of about 1% to about 20% by weight.

12. A method of treating diabetes in a patient in need thereof comprising administering the sustained-release pharmaceutical composition of claim 1.

13. A sustained-release pharmaceutical composition comprising metformin or a pharmaceutically acceptable salt thereof; and a sustained-release delivery system which comprises a hydrophilic compound selected from the group consisting of xanthan gum, deacylated xanthan gum, a carboxymethyl ester of xanthan gum, a propylene glycol ester of xanthan gum, tragacanth, pectin, acacia, karaya, alginate, agar, carageenan, gellan gum, and a mixture of two or more thereof, a homopolysaccharide compound selected from the group consisting of guar gum, hydroxypropyl guar gum, locust bean gum, and a mixture of two or more thereof; and one or more pharmaceutical diluents selected from the group consisting of monosaccharides, disaccharides, polyhydric alcohols, and mixtures of two or more thereof, wherein therapeutically beneficial blood levels of metformin are maintained over a period of time from about 1 to about 24 hours.

14. The sustained-release pharmaceutical composition of claim 13, wherein the one or more pharmaceutical diluents are selected from the group consisting of starch, lactose, dextrose, mannitol, sucrose, microcrystalline cellulose, sorbitol, xylitol, fructose, and a mixture of two or more thereof.

15. The sustained-release pharmaceutical composition of claim 13, wherein the sustained-release delivery system further comprises calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, or a mixture of two or more thereof.

16. The sustained-release pharmaceutical composition of claim 13, wherein the sustained-release delivery system further comprises an alkyl cellulose, a hydrophobic cellulosic compound, a polyvinyl acetate polymer, a polymer or copolymer derived from an acrylic acid ester and/or a methacrylic acid ester, a zein, a wax, a shellac, a hydrogenated vegetable oil or a mixture of two or more thereof.

17. The sustained-release pharmaceutical composition of claim 13, wherein the weight ratio of metformin or the pharmaceutically acceptable salt thereof to the hydrophilic compound and homopolysaccharide compound is about 1:0.1 to about 1:2.

18. The sustained-release pharmaceutical composition of claim 13, wherein the weight ratio of metformin or the pharmaceutically acceptable salt thereof to the hydrophilic compound and homopolysaccharide compound is about 1:0.3 to about 1:1.

19. The sustained-release pharmaceutical composition of claim 13, further comprising a coating which comprises a hydrophobic polymer.

20. A method for treating diabetes in a patient in need thereof comprising administering a therapeutically effective amount of a sustained-release pharmaceutical composition of claim 13.

21. A sustained-release pharmaceutical composition comprising metformin or a pharmaceutically acceptable salt thereof, and a sustained-release delivery system comprising at least one hydrophilic compound selected from the group consisting of gums, cellulose ethers, acrylic resins, polyvinyl pyrrolidone, protein-derived compounds, and mixtures of two or more thereof, at least one cross-linking agent selected from the group consisting of homopolysachharides, alginic acids, alginic acid derivatives, hydrocolloids, and mixtures of two or more thereof, and at least one pharmaceutical diluent selected from the group consisting of monosaccharides, disaccharides, polyhydric alcohols, and mixtures of two or more thereof, wherein the weight ratio of metformin or the pharmaceutically acceptable salt thereof to the at least one hydrophilic compound and the at least one cross-linking agent is from about 1:0.2 to about 1:1.5; wherein the weight ratio of the at least one pharmaceutical diluent to the at least one hydrophilic compound is from about 1:4 to about 4:1; and wherein therapeutically beneficial blood levels of metformin are maintained over a period of time from about 1 to about 24 hours.

22. The sustained-release pharmaceutical composition of claim 21, wherein the sustained-release delivery system further comprises at least one cationic cross-linking compound selected from the group consisting of monovalent metal cations, multivalent metal cations, inorganic salts, and mixtures of two or more thereof; and wherein the weight ratio of the at least one hydrophilic compound to the at least one cationic cross-linking compound is from about 1:4 to about 4:1.

23. A method for treating diabetes in a patient in need thereof comprising administering a therapeutically effective amount of the sustained-release pharmaceutical composition of claim 21.

* * * * *